United States Patent [19]
Kuhr et al.

[11] Patent Number: 5,650,061
[45] Date of Patent: Jul. 22, 1997

[54] LARGE AMPLITUDE SINUSOIDAL VOLTAMMETRY

[75] Inventors: Werner G. Kuhr, Riverside, Calif.; John K. Cullison, Burlington, Mass.

[73] Assignee: The Regents of the University of California, Oakland, Calif.

[21] Appl. No.: 529,661

[22] Filed: Sep. 18, 1995

[51] Int. Cl.$^6$ .................................................. G01N 27/26
[52] U.S. Cl. ........................... 205/775; 204/400; 204/434; 205/794
[58] Field of Search ................................ 204/400, 434; 205/775, 794

[56] References Cited

U.S. PATENT DOCUMENTS

| | | |
|---|---|---|
| 4,058,446 | 11/1977 | Zirino et al. . |
| 4,132,605 | 6/1979 | Tench et al. . |
| 4,321,322 | 3/1982 | Ahnell . |
| 4,533,456 | 8/1985 | Kratochvil et al. . |
| 4,631,116 | 12/1986 | Ludwig . |
| 4,786,373 | 11/1988 | Saloheimo et al. . |
| 4,928,065 | 5/1990 | Lane et al. . |
| 4,978,915 | 12/1990 | Andrews, Jr. et al. . |

(List continued on next page.)

OTHER PUBLICATIONS

Real–time measurement of dopamine release in rat brain; W.G. Kuhr et al., Brain Res.; 381 (1986) month unavailable 168–71.

In Vivo Voltammetry with Electrodes that Discriminate between Dopamine and Ascorbate; A.G. Ewing et al., Brain Res. 249 (1982) month unavailable 361–370.

Nicotinic Receptor–mediated Catecholamine Secretion from Individual Chromaffin Cells; David J. Leszczyszyn et al.; J. Biol. Chem 265 14736–14737 (1990).

(List continued on next page.)

*Primary Examiner*—T. Tung
*Attorney, Agent, or Firm*—Daniel L. Dawes

[57] ABSTRACT

A large amplitude sine wave is applied as the excitation potential to a amperometric measurement to produce a current output that is a phase shifted sine wave containing faradaic information at many frequencies. A current obtained from a conventional potentiostat coupled to the electrode is coupled to a lock-in amplifier that monitors the signal at one frequency at a specified phase angle. Since most of the background remains at the fundamental frequency, a higher harmonic of the fundamental frequency of the sinusoidal sweep frequency is monitored. By locking in on the higher harmonic components, the faradaic signal is therefore distinguished from the background signal. The background is diminished thereby allowing signal recognition at low analyte concentrations and increasing the signal-to-noise ratio.

13 Claims, 7 Drawing Sheets

U.S. PATENT DOCUMENTS

| | | |
|---|---|---|
| 5,071,527 | 12/1991 | Kauffman . |
| 5,124,011 | 6/1992 | Rogers et al. . |
| 5,131,999 | 7/1992 | Gunasingham . |
| 5,192,403 | 3/1993 | Chang et al. . |
| 5,217,112 | 6/1993 | Almon . |
| 5,223,118 | 6/1993 | Sonnenberg et al. . |
| 5,292,423 | 3/1994 | Wang . |
| 5,296,123 | 3/1994 | Reddy et al. . |
| 5,324,400 | 6/1994 | Eliash et al. ............................ 204/434 |

OTHER PUBLICATIONS

Recent Advances in Pulse Cyclic and Square–Wave Cyclic Voltammetric Analysis., Gordon N Eccles. Crit. Rev. Anal. Chem. 22, 345–80 (1991) month unavailable.

Oscillographic Polarography at Controlled Alternating Current; Heyrovsky et al., date unavailable.

Studies on Alternating Current Electrolysis, Remick et al, J. of the Electrochemical Soc., Jul. 1962, pp. 628–634.

Microvoltammetric Electrodes. Wrightman et al; Ana. Chemistry vol. 53, No. 9, 19881 month unavailable.

Hanekamp et al., "Applicability of Phase–sensitive Alter. Current Measurements in Flow–through Detection," Anal. Chim. Acta, v131, pp. 149–158, 1981 month unavailable.

Kingsley et al., "Exp'tal Study of Phase–Sensitive ac Voltammetry in Continuous–Flow Streams–Reversible Systems," Electroanalysis, 2, pp. 273–277, 1990 month unavailable.

Curran, et al., "Instrument for Altern. Current–Voltammetry Featuring a Digital Phase–Sensitive Detector: Applic. to Flow–Inj. Anal. using ac Amperometry," Electroanalysis, 2, 435–442, 1990 month unavailable.

Long et al., "Voltammetry in Static & Flowing Solutions w/a Large–Amplitude Sine Wave Potential," Electroanalysis, v4, pp. 429–437, 1992 month unavailable.

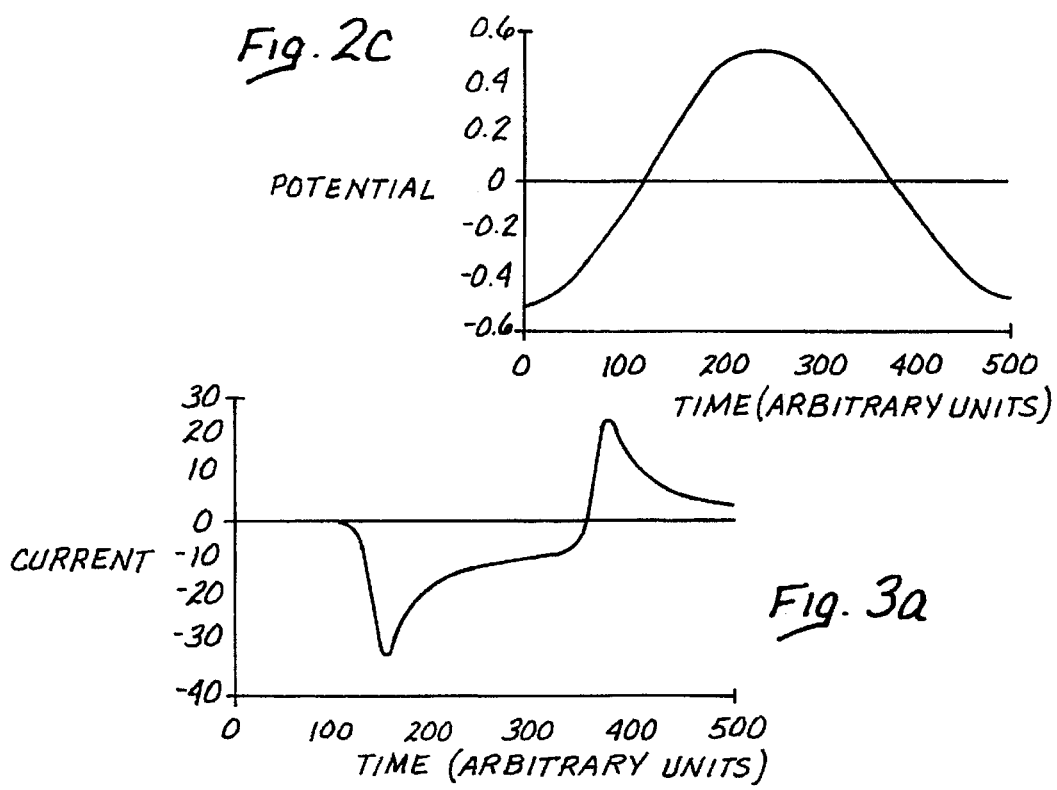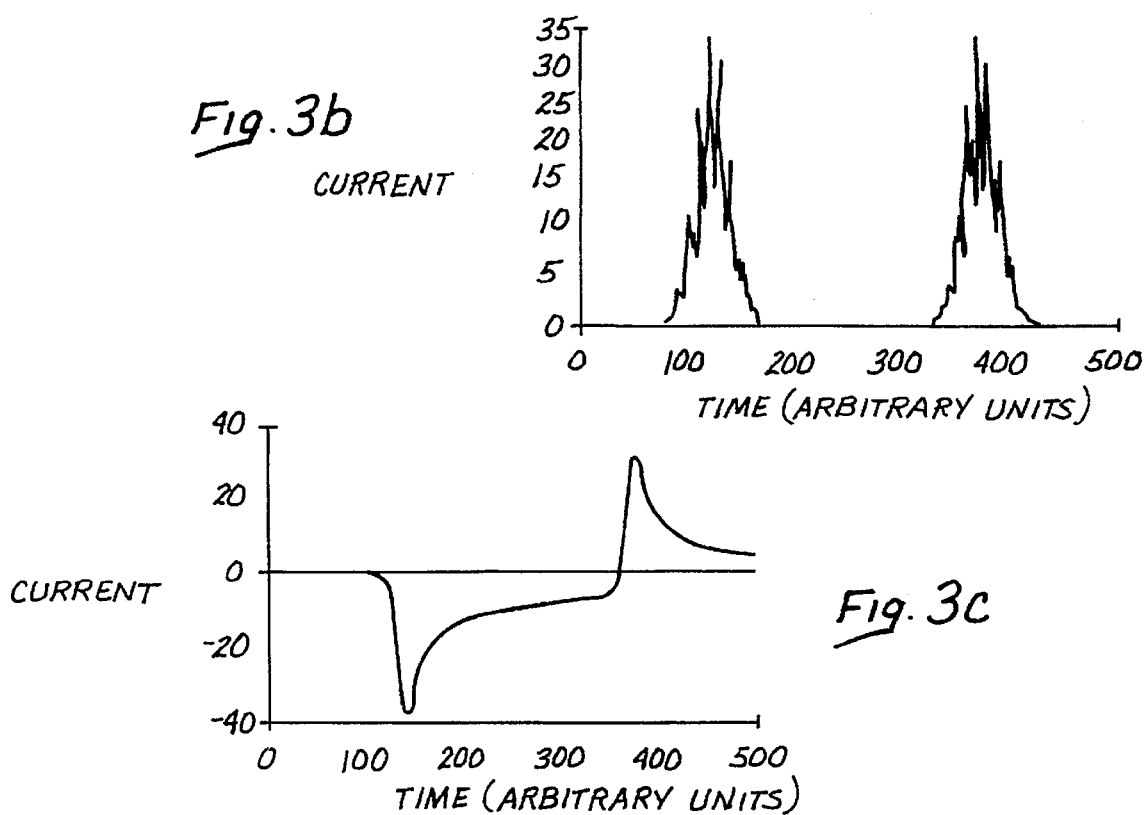

LARGE AMPLITUDE SINUSOIDAL VOLTAMMETRY

This invention was made with Government support under Grant No. CHE8957394, awarded by the National Science Foundation. The Government has certain rights in this invention.

BACKGROUND OF THE INVENTION

1. Field of the Invention

The present invention relates to sinusoidal voltammetry with either lock-in detection or Fourier Transform based computer methods as an electroanalytical method for making fast, very small volume chemical analyses of a fluid.

2. Description of the Prior Art

Several electroanalytical techniques have been developed for measurement of small volumes of fluid in short time periods, such as a few hundred milliseconds. For example, fast scan voltammetry is described by W. G. Kuhr et.al., Brain Res. 381 at 168–71 (1986). Chronoamperometry is described by A. G. Ewing et.al., Brain Res. 249 at 361–70 (1982). DC amperometry is described by D. J. Leszczyszyn et al., J. Biol. Chem., 265 at 1473–7 (1990). These methods have been used for the measurement of various electroactive neurotransmitters, such as dopamine, norepinephrine and serotonin, to ascertain the kinetics of release and uptake process in vivo in the mammalian brain on a subsecond time scale.

In particular, electrochemical detection at carbon fiber microelectrodes with fast cyclic voltammetry has been used successfully for the characterization of dopamine release and uptake in vivo as described by R. M. Wightman, Anal. Chem. 53 at 1125a–30a (1981) and W. G. Kuhr et.al., Brain Res. 381 at 168–71 (1986). The fast scan rates, i.e. 100 to 300 volts per second, provide excellent temporal resolution and enhanced selectivity over compounds that have slower electron transfer kinetics than the analyte of interest. The use of Nation coated microelectrodes has improved the limits of detection to the order of 50 nM for dopamine when used in combination with signal processing and sampling methods.

Additional improvements in sensitivity in fast scan cyclic voltammetry have been gained through improvement to signal processing and sampling strategies. While voltammetry has also been used to monitor secretion of catecholamines from individual cells on millisecond time scales, DC amperometric recordings have been found to give better signal quality. Similar trends are found when electrochemical detection was used in combination with separation methods, e.g. HPLC, capillary LC and capillary electrophoresis. DC methods generally have better sensitivity because of the bandpass of the measurement is narrower, that is low pass filtering reduces the high frequency noise and there is a virtual absence of background currents.

Traditionally, electrochemical methods generally improve the signal-to-noise ratio by discriminating the faradaic signal from the background components in the time domain through application of pulsed waveforms, i.e. differential pulse polarography and square wave voltammetry. Pulse methods are able to discriminate the faradaic current from the charging current in the time domain. Since charging currents decay much more rapidly than faradaic current, i.e. exponentially as compared to the inverse square root. However, the analytical faradaic current is not totally discriminated from the charging current and most of the signal is discarded because sampling must be done late in the pulse cycle. Even under these conditions, limits of detection on the order of $10^{-8}$M can be obtained with pulsed methods, albeit at the cost of analysis time, typically at 10 to 100 seconds per scan.

Alternatively, modulation techniques have been used to great effect in a number of circumstances to improve signal-to-noise ratios. In these techniques, the signal is imposed on a modulated carrier wave, such as a sine wave. The modulation frequency can be chosen to move a signal into a region of the frequency spectrum where there are minimal noise contributions. This is particularly useful for detection of species in real time on a subsecond time scale where 1/f noise is often a problem. Often, a lock-in amplifier is used in modulation methods to decrease the bandwidth of the monitored signal to discriminate the signal from the noise on the basis of frequency and phase. The decreased bandwidth serves to reduce noise, enhance signal recognition and increase the signal-to-noise ratio.

The frequency domain has only been used in a few electroanalytical techniques to enhance the signal-to-noise ratios in electrochemical analysis. In AC voltammetry, a potential ramp is applied to the electrode, typically 10 to 15 millivolts per second, and a small amplitude sine wave, typically less than 50 millivolts, usually on the order of 10 millivolts, is superimposed onto the linear ramp. Measurement of the fundamental and harmonic frequencies are taken using a lock-in amplifier. Small amplitude modulations are used to minimize the nonlinear effects and enhance resolution. The scan time is determined by the slope of the linear ramp. The time of analysis typically various from 20 to 200 seconds per scan. Since the potential is modulated at 100 to 1,000 times the fundamental frequency of the ramp, modulation frequencies are typically on the order of ten to hundreds of Hertz. See for example, Eccles, Crit. Rev. Anal. Chem. 22 at 345–80 (1991).

While small amplitude modulation works well at a large electrode at conventional scan rates, that is electrodes of millimeter dimensions with scan rates in the range of 10 to 50 millivolts per second with a corresponding time analysis of 20 to 200 seconds, it would be difficult to implement this type of modulation strategy at scan rates fast enough to provide information relevant to neurotransmission. For example, the measurement of stimulated dopamine released in a rat brain, scan rates of 300 volts per second are commonly employed with a complete scan obtained in less than 10 milliseconds. Thus, to maintain adequate potential resolution in AC voltammetry, one would have to use the modulation frequency in excess of 100 kHz. Similarly, it would be difficult to use pulse methods to make a complete voltammetric measurement on a millisecond time scale. Either the period of the step would be too short to allow discrimination against charging current, e.g. 10 microseconds per step, or the number of potential steps must be reduced which would limit resolution.

There are no neurochemical molecules which have electron transfer kinetics fast enough to allow this modulation frequency. Therefore, any methods requiring multiple potential steps, such as chronoamperometry, pulse voltammetry or square wave voltammetry or potential modulation such as AC voltammetry, will be difficult to implement to measure these dynamic chemical phenomena.

Sinusoidal voltammetry, an analog of continuous scan cyclic voltammetry, uses a large amplitude sinusoid exclusively as the potential waveform. An analog of this method was originally called "oscillographic polarography" and predates the use of linear scan techniques as currently used in cyclic voltammetry. See M. Heyrovsky et al., in Electroanalytical Chemistry: A Series of Advancements, Marcel Dekker, Inc., New York, Volume 2 at 193–56 (1967). The use of a triangular wave in a cyclic voltammetric experiment gained favor over the use of a sine wave because of the theoretical complications imposed by the fact that in the case of a sine wave the scan rate is continuously changing throughout the duration of the experiment. While the experimental equivalent to steady state sinusoidal voltammetry has been mathematically described, little work has been done in this field over the last 20 years. See A. E. Remick et al., J. Electrochem. Soc. 109 at 628–34 (1962).

A sinusoidal waveform has been used to simplify digital filtering in the frequency domain for voltammetric analysis. See J. T. Long, Electroanalysis 4 at 429–37 (1992). It was found that the sinusoidal waveform produced better signal-to-noise ratios when using digital filter routines in flow injection analysis experiments. Fourier transform methods have been used to examine many of the properties of different electroanalytical experiments, but the analytical advantage of this technique has not been exploited.

Most electrochemical methods rely on differences between the formal potential (half widths) of compounds present in a sample to generate the selectivity for measurement which leads to an effective resolution of only 6 to 10 components. In practice, this has severely limited the utility of electrochemical methods for the analysis of many complex matrices. Additional selectivity could be obtained only through the use of other electrochemical methods to clean up the sample prior to electroanalysis or the addition of ion-selective membranes to the electrode surface to alter the transport of the sample constituents to the electrode surface. What is needed then is a method for using large amplitude sinusoidal waveform in fast electroanalytical tests.

Therefore what is needed is some methodology which can exploit the vast diversity in electron transfer rates observable at solid electrodes to obtain additional selectivity in the electrochemical measurement.

BRIEF SUMMARY OF THE INVENTION

The invention is a method for making a fast electrochemical analysis of a small volume of analyte having at least one redox species of interest with a formal potential included within a potential window. The method comprises the steps of providing a small amount of the analyte to a voltammetric electrode, which typically may be part of a flow injection analysis cell or chromatographic detector. A sinusoidal sweeping voltage is applied to the electrode. The sinusoidal voltage has an amplitude large enough to sweep through the formal potential of the redox species of interest in a single cycle at a given frequency, henceforth defined as the fundamental frequency. The response of the analyte to the sinusoidal voltage is selectively detected at a harmonic of the fundamental frequency of the sinusoidal voltage rather than at the fundamental frequency. As a result, a complete frequency spectrum can be obtained within one cycle of the sinusoidal voltage.

The step of selectively detecting the voltammetric response comprises the step of selectively detecting a current flowing through the analyte at a harmonic of the fundamental frequency. Preferably the harmonic comprises at least one harmonic of the current above the fundamental frequency. Typically, the signal is monitored at harmonics at and above the second harmonic of the fundamental frequency. In general, the step of selectively detecting the voltammetric response comprises the step of detecting a plurality of higher harmonics of the fundamental frequency within a frequency spectrum of a current flowing through the analyte, either through the use of multiple lock-in detectors, or via data acquisition in the time domain, followed by Fourier transformation and convolution via computer based methods.

The sinusoidal voltage has an initial potential and a switching potential which serve as bounds for the potential window. The method further comprises adjusting the potential window so that the formal potential of the redox species of interest of the analyte is set near the switching potential to thereby produce higher signal levels within higher harmonics of the fundamental frequency.

The step of selectively detecting the voltammetric response comprises detecting a current from the analyte at a selected phase angle of measurement to enhance a detected signal corresponding to the redox species of interest.

In addition the step of selectively detecting the voltammetric response uses the natural distortion of the rate of electron transfer between the analyte and the electrode to enhance a detected signal corresponding to the redox species of interest of the analyte. Varying the rate of electron transfer is accomplished by specific preparation of the surface and/or composition of the electrode.

The step of selectively detecting the voltammetric response comprises the step selecting a harmonic of the fundamental frequency of the sweeping sinusoidal voltage to enhance a detected signal corresponding to the redox species of interest of the analyte. The phase and frequency are both selected to enhance a detected signal corresponding to the redox species of interest of the analyte.

The invention is also an apparatus for performing fast scan electrochemical analysis of small volumes of analyte comprising a function generator for selectively providing a sweeping sinusoidal voltage. An electrode is coupled to the function generator for coupling the sweeping sinusoidal voltage to an analyte at a fundamental frequency. A circuit is provided for selectively detecting a voltammetric response at the electrode from the analyte in response to the sweeping sinusoidal voltage. The sinusoidal voltage is generated by the function generator and has a magnitude sufficient to sweep through the formal potential of the analyte within a single cycle. As a result, fast scan electrochemical analysis of the analyte is achieved.

The instrument detects the voltammetric response in the frequency domain, where all the information is processed. This is accomplished in real time with a lock-in amplifier, which is set to measure the signal at a specified frequency and phase angle with respect to the excitation waveform. The amplitude and frequency of the excitation waveform is determined by the electrochemical properties of the analyte as well as the background signal, so as to maximize the signal due to the analyte at higher harmonics while minimizing the contribution to the background currents in the same frequency regime. Detection frequency and phase angle are determined by examining the frequency spectrum of the analyte and finding the harmonic at which the analyte has the highest signal-to-noise ratio. The phase angle is determined by maximizing the signal magnitude while minimizing the contributions due to the background.

Alternatively, the voltammetric response can be converted into a digital signal via a fast, high-resolution analog-to-digital interface to a computer. Following acquisition of the response, digital data processing techniques can be used to convert the time domain data into frequency-domain data. One such process, commonly referred to as Fourier Transformation, uses a digital fast-Fourier transform to generate a frequency spectrum of the voltammetric response, which comprises the magnitude and phase of each frequency element. The Fourier transform is performed at least once and preferably repeated at periodic intervals so as to collect frequency spectra of the signal and background as a function of time. Digital processing techniques can then be used to isolate the signal form the background in the frequency domain.

The invention may now be better visualized by turning to the following drawings wherein like elements are referenced by like numerals.

BRIEF DESCRIPTION OF THE DRAWINGS

FIGS. 2a–2c show the scanning potential waveforms in the time domain used for cyclic voltammetry, AC voltammetry and large sinusoidal voltammetry respectively.

FIGS. 3a–3c are the current responses in the time domain corresponding to the waveforms of FIGS. 2a–2c respectively.

FIGS. 5a and 5b show both the background response and the response upon the addition of ferrocene.

The invention and its various embodiments may now be better understood by turning to the following detailed description.

DETAILED DESCRIPTION OF THE PREFERRED INVENTION

A large amplitude sine wave is applied as the excitation potential to an amperometric measurement to produce a current output that is a phase shifted sine wave containing faradaic information at many frequencies. A current obtained form a conventional potentiostat coupled to the electrode is coupled to a lock-in amplifier that monitors the signal at one frequency at a specified phase angle. Since most of the background remains at the fundamental frequency, a higher harmonic of the fundamental frequency of the sinusoidal sweep frequency is monitored. By locking in on the higher harmonic components, the faradaic signal is therefore distinguished from the background signal. The background is diminished thereby allowing signal recognition at low analyte concentrations and increasing the signal-to-noise ratio.

Figure 1:
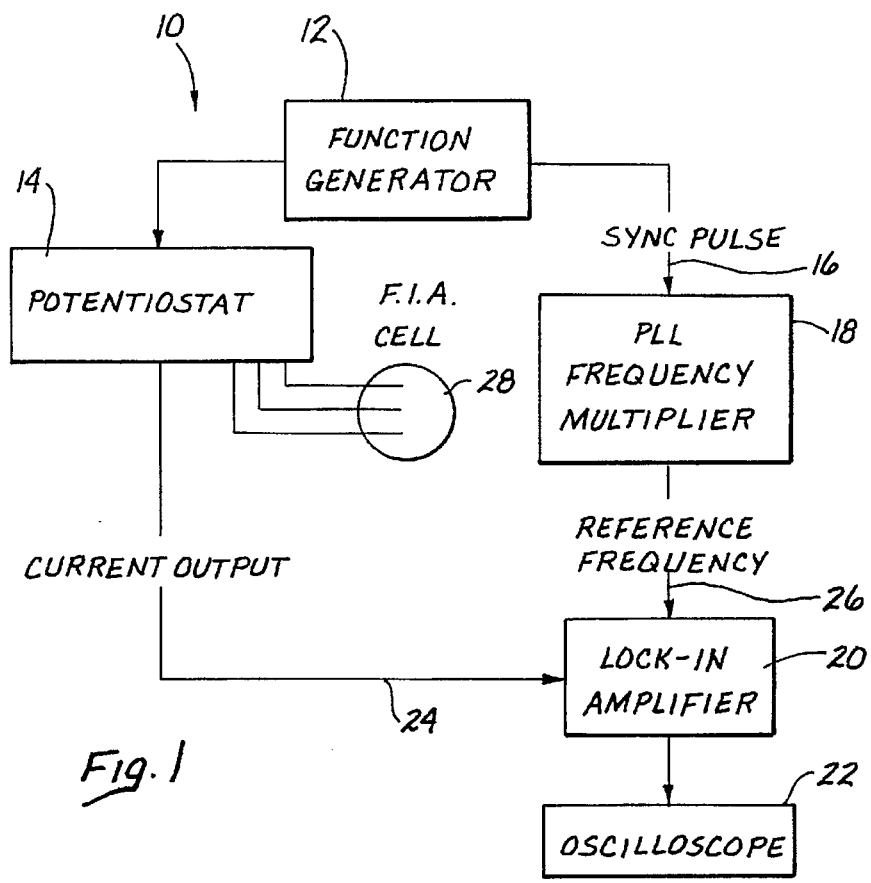
FIG. 1 is a simplified block diagram of the system in which flow injection analysis according to the invention can be practiced.

FIG. 1 is a simplified block diagram of the system in which flow injection analysis according to the invention can be practiced. The apparatus of FIG. 1 has been essentially described in connection with a different methodology by W. G. Kuhr et al., Anal. Chem. 65 at 617–22 (1993).

The flow injection system, generally denoted by reference numeral 10 includes a function generator 12 to generate a sine wave excitation waveform which is coupled to potentiostat 14. Function generator 12 also provides a TTL synchronization pulse to input 16 of frequency multiplier 18. Frequency multiplier 18 includes a variable switch to allow access to integral frequency harmonics of up to 10 times the frequency of the fundamental provided by frequency generator 12. The output of phase lock loop frequency multiplier 18 provides a TTL reference frequency input pulse to lock-in amplifier 20. The output of lock-in amplifier 20 may be monitored, for example, by an oscilloscope 22. The current output of potentiostat 14 is provided to input 24 of lock-in amplifier 20. Lock-in amplifier 20 cross-correlates the input signal on line 24 with the reference frequency on line 26, the integrated or filtered output is digitized, stored and displayed on oscilloscope 22.

Potentiostat 14 is coupled to a conventional fluid injection analysis cell 28. A commercial 10 micron diameter gold disk microelectrode, such as manufactured by Bioanalytical Systems Inc. of West Lafayette, Ind., is polished with 1 micron water based diamond polish followed by ¼ micron diamond polish. The electrodes are then sonicated in hot toluene for 10 seconds followed by sonication in water for 10 seconds to remove residual polishing materials.

Alternatively, carbon fiber microelectrodes are fabricated in 4-inch long glass capillaries pulled using a microelectrode puller. Ten micron or 32 micron carbon fibers were aspirated into the tapered tips of the pulled capillaries and epoxy is applied under a microscope to the tip of the capillary. Care is taken to assure that the exposed carbon fiber surface does not come into contact with the epoxy. Cylindrical carbon fiber electrodes are then cut to a length of approximately 500 microns with a scalpel.

Still further, a 10 micron diameter disk electrode is made as described above except after aspiration, it is dipped into epoxy containing 12 to 14 percent hardener. The electrodes are cured in an oven overnight at 60 degrees centigrade and then polished to a beveled tip with 1 micron diamond polishing compound. Prior to use, the electrodes are sonicated for 10 seconds in hot toluene and then sonicated for 10 seconds in deionized water. The 10 micron disk electrodes are electrochemically pretreated by cycling between −0.2 to 1.8 volts with a silver, silver chloride electrode at a frequency at 50 Hertz for 3 seconds. Electrochemical activation has been observed to enhance heterogeneous electron transfer rate constants and increase the magnitude of the faradaic response for certain cationic species. A silver/silver chloride reference electrode is used in all aqueous experiments and a platinum wire functions as a counterelectrode in all case.

A solenoid driver circuit allows computer control of a compressed air driven valve which switches flow from a buffer loop to a sample loop in flow injection and analysis (FIA) cell 28. Cell 28 is constructed from Plexiglas in such a way as to allow the microelectrode to be positioned about 60 millimeters from the output of the FIA sample loop. The cell was designed to match the internal diameter of the FIA tubing, i.e. 0.75 millimeters, in order to minimized diffusional broadening of the analyte as it was transported to the microelectrode, which is important for the measurement of a subsecond response times. The flow rate of approximately 0.81 milliliters per minute was controlled by a syringe pump or by gravity flow.

The electrochemistry is performed using either a two or three electrode potentiostat. The current output of potentiostat 14 is provided to the input 24 of lock-in amplifier 20.

The method of the illustrated embodiment is described in connection with voltammetry of ferrocene and hexamine ruthenium chloride. Voltammetry of ferrocene is conducted using a 10 micro diameter gold microelectrode. The concentration of ferrocene is 1.3 microMoles and 0.5M tetrabutylammonium perchlorate (TBAP) in acetonitrile which is used as electrolyte/solvent system. In the illustrated embodiment the width of the potential window is 0.5 volts and the scan frequency is 400 Hertz. The potential window is varied about the formal potential of ferrocene while keeping the amplitude and scan frequency the same. Data is collected on the oscilloscope, stored on disk and transferred to a 486 personal computer for data processing. The background current is subtracted using Quatro Pro for Windows as manufactured by Borland International, California.

The voltammetry of hexamine ruthenium (III) chloride is performed using carbon fiber barrel electrodes. A two hundred twenty-five microMoles solution of hexamine ruthenium chloride at 32 micron carbon barrel electrodes using a 0.15M potassium chloride, 7.4 pH, and 50 microMoles phosphate buffer were used. The switching potentials were at −0.1 and 0.9 volts versus Ag/AgCl reference. The frequency of the sinusoid was 10 Hertz. The current was monitored as a function of the phase angle for both background and faradaic currents.

In both of these embodiments, sinusoidal voltammograms were obtained by providing a sine wave excitation from function generator 12 to potentiostat 14. The current from potentiostat 14 was sampled through lock-in amplifier 20 by oscilloscope 22, data was stored and processed in a personal computer. Linear sweep cyclic voltammetry was conducted in a similar fashion except that the conventional cycle potential ramp was applied as an excitation waveform instead of a sinusoid. A bandpass filter on the lock-in amplifier input 24 was set to the frequency of the external reference from function generator 12. The output of lock-in amplifier was filtered with a low pass filter with a time constant set to either 1 second or 300 milliseconds. Filtering prior to the lock-in amplifier affected the phase of the signal at higher harmonics.

Care was taken to avoid the effects of aliasing and leakage. Aliasing was avoided by taking the data at a rate of 40 times the fundamental frequency of the excitation waveform. The analog signal was filtered at 20 kHz, which was the RC time constant in potentiostat 14, and digitized with 12 bits of resolution. Additional filtering was avoided to minimize the phase shift of any current measuring circuits. In most cases, the signal appeared to have minimal power distributed at frequencies approaching the Nyquist frequency. Leakage or loss of low frequency signals due to limited resolution arising from the bandwidth of signal acquisition was avoided by sampling a wide bandwidth of at least 4,000 data points. In most cases, over 20 continuous scans were obtained in a single measurement. Acquiring a larger number of scans increased the resolution at lower frequencies, and a longer sampling time minimized artifacts due to the convolution of the window function with the data. The data was analyzed and processed in a 386 personal computer. Fourier transforms were performed using Mathcad, manufactured by Mathsoft Inc. of Massachusetts. The magnitude was determined from the real and imaginary components of the discrete Fourier transform of the signal. In some cases, the magnitude was normalized versus the magnitude of the fundamental frequency.

The current response to a sinusoidal waveform was modelled on a quasireversible electron transfer reaction mechanism, namely O+ne=R, where O is the oxidizing agent, n the number of electrons transferred, and R the reducing agent. This model is described by conventional equations for semi-infinite linear diffusion as defined by Fick's 2nd Law under conditions where only the oxidizing agent is initially present. The solution for the current, which results from these equations, shows that the contribution to the current from high order harmonics decreases when the amplitude of the sinusoid is kept below about 0.050 volts.

Thus, in conventional AC voltammetry, the objective is to look only at the lower order harmonics since only these terms materially contribute the current. This allows a theoretical solution to be simply provided and described by the DC and lower harmonic components with substantial accuracy as long as the amplitude of the driving sinusoid is less than about 50 millivolts and the frequency of the sinusoid is significantly higher than the DC scan rate, typically 100 to 1,000 times the frequency of the effective scan rate, since the DC offset voltage is assumed to be a constant potential. Under these conditions, the current of the fundamental harmonic appears as a first derivative of the DC current yielding a characteristic peak-shaped curved.

When larger sinusoidal amplitudes are used to drive the flow injection cell, much of the signal is distributed to the high order harmonics, which are also higher order differentials. Thus, the integral equation becomes much more difficult to evaluate since the integrals for any higher order terms contain all the lower order terms as well. The prior art has evaluated these expressions up to the fifth harmonic, but no one has evaluated the full frequency spectrum.

It is to be understood according to the present invention that the current is distributed over integral harmonics of the fundamental frequency and that the magnitude of the higher harmonics falls off rapidly. An analytic solution is extremely difficult, although numeric solutions can be calculated.

Figure 2A:
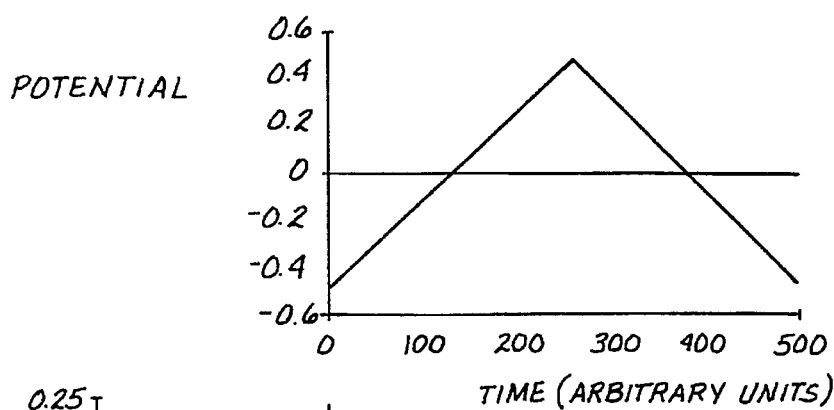
Figure 2B:
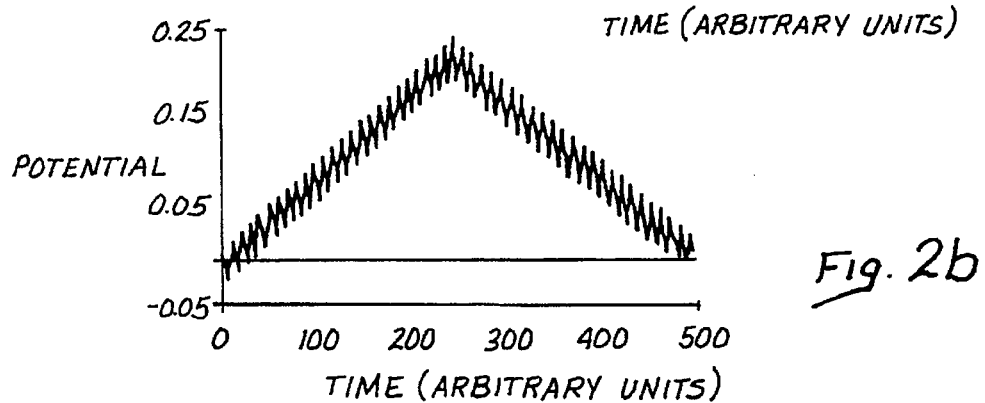
Figure 4A:
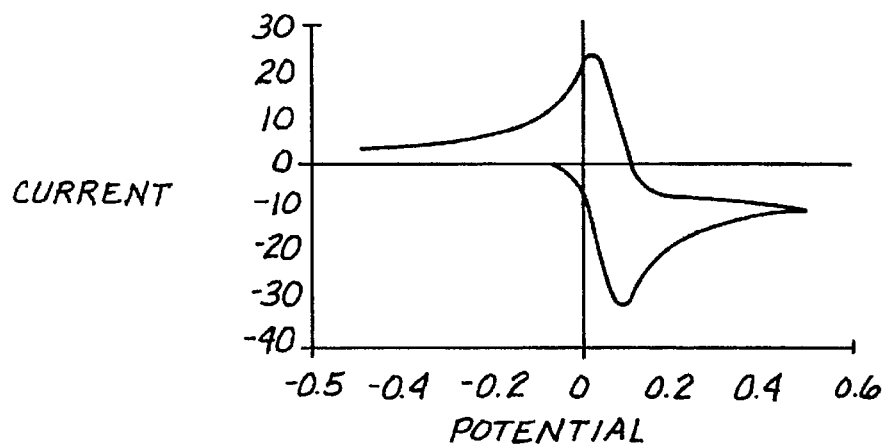
FIGS. 4a–4c are the voltammetric plots of the respective current responses shown in FIGS. 3a–3c shown with the current on the y axis and the potential on the x axis.
Figure 4B:
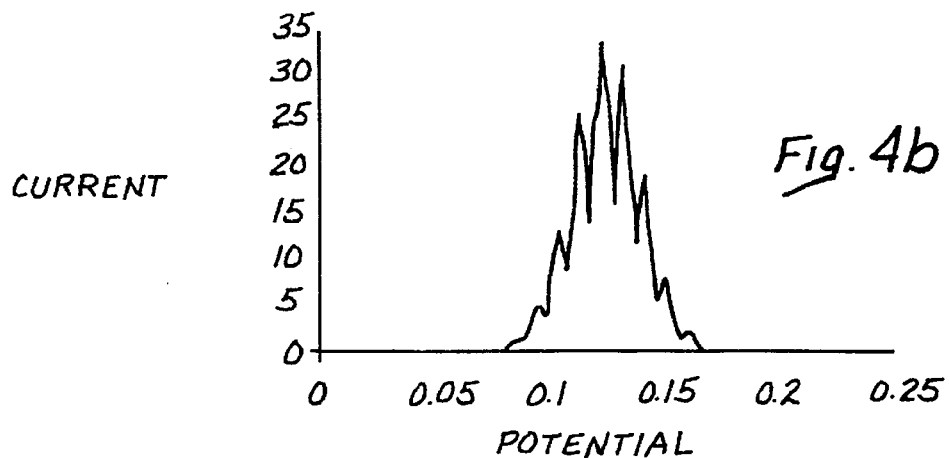
Figure 4C:
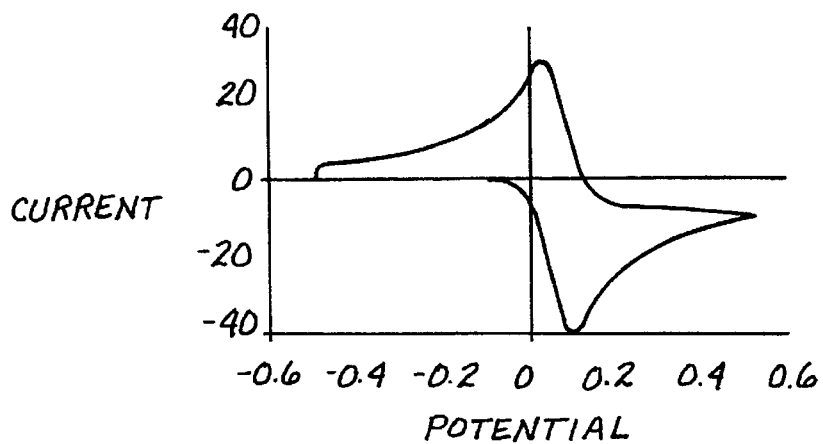

FIGS. 2a–2c illustrate the difference between large amplitude sinusoidal, and prior art cyclic and AC voltammetry. FIGS. 2a–2c are simplified potential waveforms showing the waveform of the excitation voltage applied to the flow injection cell with voltage graphed on the vertical scale against time in arbitrary units across the horizontal scale. Sinusoidal voltammetry as described here is an analog of continuous scan cyclic voltammetry where sine wave is used in place of a triangular wave.

As illustrated, the current response as can be seen by a comparison of FIGS. 3a and 3c in sinusoidal voltammetry in the time domain is very similar to the current response observed in cyclic voltammetry. FIG. 3b illustrates the current response for AC voltammetry. The major difference between the current response in FIG. 3a for cyclic voltammetry and that shown in FIG. 3c for sinusoidal voltammetry is that the scan rate is continuously changed throughout the duration of the waveform in the case of sinusoidal voltammetry. The rate of change of the potential sweep, called the scan rate in linear sweep voltammetry, is equivalent to the frequency of the sinusoid which is defined as the scan frequency. This allows a digital simulation of sinusoidal sweep of voltammetry since the applied potential can be calculated incrementally as a sinusoid and the instantaneous scan rate can then be calculated exactly as a first derivative of the applied potential at any point in time.

AC voltammetry utilizes a small amplitude sine wave which is added to a potential ramp to modulate the current output as shown in FIG. 2b. Typically, modulation potential amplitude of up to 20 millivolts is used with higher amplitudes being avoid in order to avoid contributions from higher order harmonics. Therefore, small amplitude modulations, typically about 10 millivolts, are used to minimize the nonlinear effects and to enhance resolution. This may be thought of as a limiting case for sinusoidal voltammetry since all of the information is intentionally contained in only the lowest order harmonics in AC voltammetry. The scan rate, and hence the analysis time, is determined by the slope of the linear ramp and potential must be modulated at 100 to 2,000 times the fundamental frequency of this ramp to maintain sufficient voltammetric resolution. Thus, the linear scan rate, which is typically 1 to 100 millivolts per second, determines the analysis time which is generally the order of 20 to 200 seconds in the case of AC voltammetry.

Current measurements of the fundamental and second harmonic frequencies can be obtained using a lock-in amplifier as shown in FIG. 1, but the superposition of small amplitude modulation produces a differential response at the fundamental frequency and all higher order frequencies act as higher order differentials.

In contrast, the use of a large amplitude sinusoid as the excitation waveform as shown in FIG. 2c obviates the need for DC ramp to obtain potential resolution. Instead, all the faradaic information is contained within one period of the sinusoid whose amplitude is large enough to sweep through the redox process of interest, just as the linear scan sweeps through the appropriate potential range in linear scan voltammetry as shown in FIG. 2a. Therefore, this technique in this aspect more closely resembles cyclic voltammetry and it is therefore possible to measure on a very short time scale as it is with fast scan cyclic voltammetry.

Figure 5A:
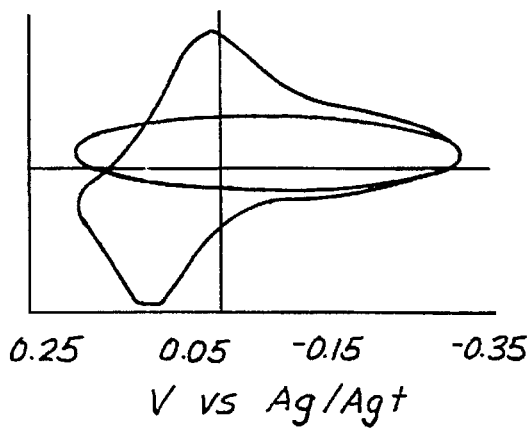
FIGS. 5a and 5b are the sinusoidal voltammogram and the cyclic voltammogram respectively for 1.3 microMoles ferrocene at a 10 micron gold microelectrode at a scanning frequency of 400 Hz using 0.6M tetrabutyl ammonium perchlorate/acetonitrile as an electrolyte/solvent system.
Figure 5B:
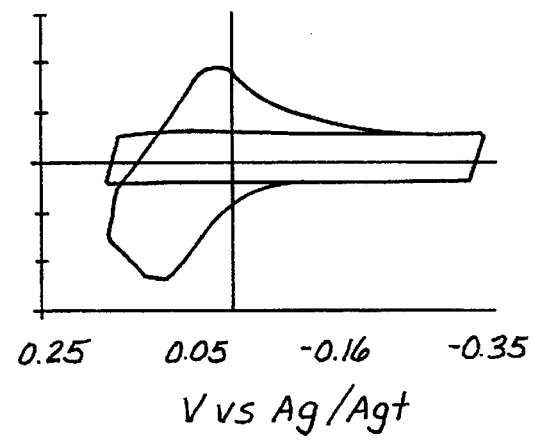

The faradaic response obtained using both triangular wave and sine wave excitation wave forms have similar frequency elements. They both possess harmonic frequency components which depend on many of the same voltammetric parameters. Response observed for the oxidation of 1.3 microMoles ferrocene in 0.5M TPAB/acetonitrile at a 10 micron gold microelectrode after application of a sinusoidal potential as shown in FIG. 5a is very similar to that observed at a conventional linear sweep as shown in FIG. 5b. Current response as shown in FIGS. 5a and 5b demonstrates the similarity of sinusoidal voltammetry to cyclic voltammetry.

An interesting difference between the two is the dependence of the peak current on the position of the half potential within the potential window when a sinusoidal waveform is used. In conventional linear sweep voltammetry, the peak shape is virtually independent of the position of the half width within the potential window, since the scan rate is constant. Since the sinusoidal waveform has an effective scan rate that is continuously changing, the instantaneous current is proportional to the instantaneous scan rate and the current will be lowest where the slope of potential waveform is lowest. Thus, a diminished peak current is observed as the formal or half wave potential, approaches the switching potential, i.e. the potential where the triangular peak occurs.

The most striking difference between conventional linear sweep and sinusoidal voltammetry is seen in the background current. The cyclic voltammogram resulting from a triangular waveform has a relative sharp current versus time transient at the switching potential. The transient contains odd harmonic components similar to those observed in a square wave pulse as shown in FIG. 6b. The frequency composition of the background current for the linear sweep voltammogram shows considerable power at the higher harmonics, and in particular, at the odd harmonic frequencies.

Figure 6A:
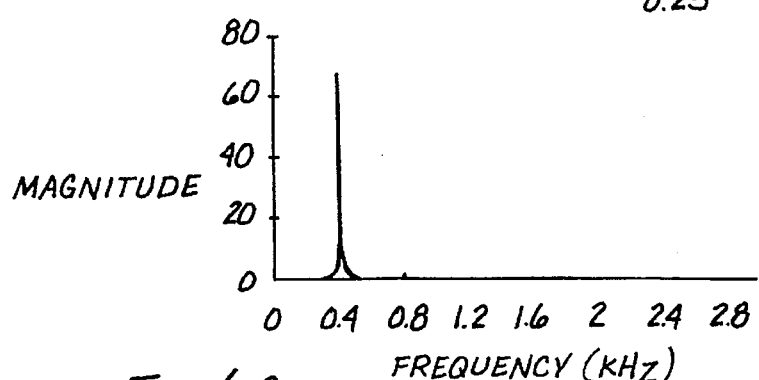
FIGS. 6a and 6b are the frequency spectra showing the background responses of the sinusoidal voltammetry and conventional scanning cyclic voltammetry respectively in the frequency domain.
Figure 6B:
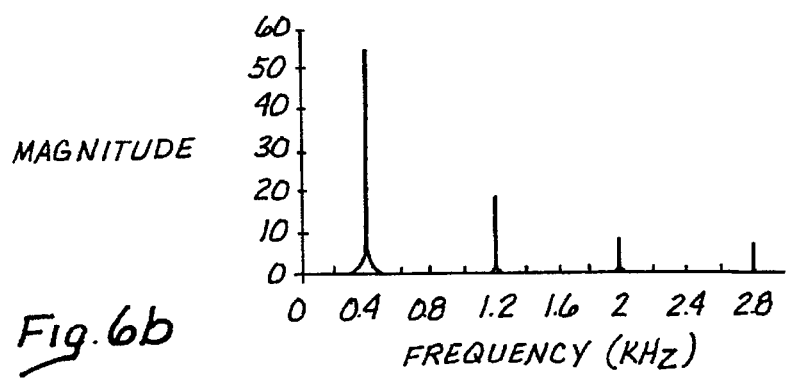

When a sinusoidal potential waveform is used, the background current, which in this case consists almost entirely of charging current, is a sinusoid at the same frequency as the excitation waveform as shown in the voltammogram of FIG. 6a. This occurs because the electrode behaves as a linear element, i.e. as a capacitor, in an RC circuit under ideal conditions. Thus, a sinusoidal excitation waveform produces a charging current that is essentially a sine wave which leads the potential by 90 degrees and has its power concentrated at the fundamental scan frequency. In most cases, the background current contains other components due to non-idealities in the sine wave, background faradaic processes, and potential dependent double layer capacitance. The magnitudes of these higher frequency components, however, are over two orders of magnitude less than that found at the fundamental frequency. Thus, the background current at the higher frequency harmonics observed in sinusoidal voltammetry is significantly smaller than that observed using linear sweep voltammetry.

Figure 7A:
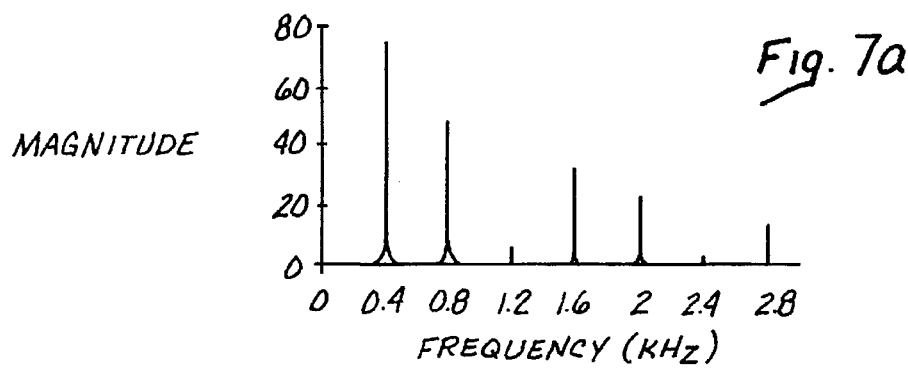
FIGS. 7a and 7b are the frequency spectra of ferrocene for sinusoidal voltammetry and conventional cyclic voltammetry respectively.
Figure 7B:
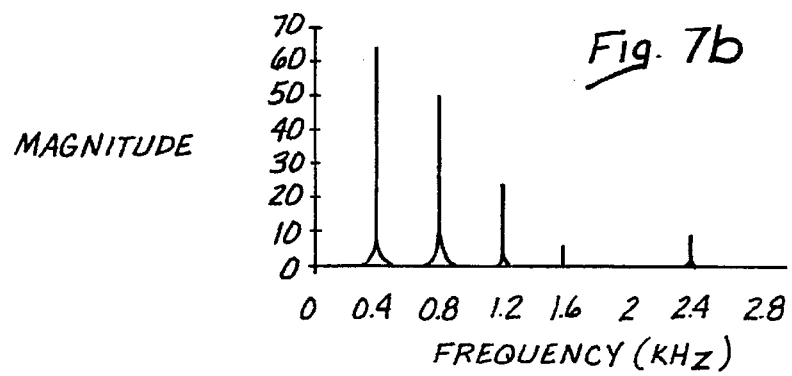

The faradaic current in contrast has a large part of its signal intensity at the higher frequency harmonics in both linear and sinusoidal voltammetry as depicted in FIGS. 7a and 7b. This results from the nonlinear relationship between current and over potential as described by Butler-Volmer Kinetics. Since the magnitude of faradaic current is determined by both electron transfer and mass transfer kinetics, the relationship of current dependence on potential for the diffusion-limiting case can be quite complex. When large sinusoidal waveforms are employed and the frequency of the waveform is rapid enough to deplete the diffusion layer, the solution to the diffusion equations is even more intractable than for linear sweep voltammetry.

Analysis of the integration of the standard differential equation for semi-infinite linear diffusion as defined by Fick's 2nd Law is according to the invention the right point from which to begin to seek the solution. While it is extremely difficult to obtain an analytical expression for this function for a large amplitude sinusoid, considerable insight into the relative magnitudes of the harmonic frequency components generated by the excitation waveform is obtained by expansion of the differential equation. This results in a Fourier series composed of sine and cosine terms at odd and even frequency harmonics, respectively. Thus, all the faradaic information is encoded into these harmonics and the magnitude and phase of each component depends on the same electrochemical parameters as in linear sweep voltammetry, for example overpotential, scan rate and the like.

Studies of the sinusoidal voltammograms and frequency spectra of the invention have revealed that when the formal potential is centered in the potential window, the voltammetry is well defined and the frequency spectrum is composed of odd harmonic frequencies. As the formal potential is moved toward $E_{switch}$, there is little change in the appearance of the voltammetry, while there is a dramatic change in the distribution of intensities in the frequency spectra. Both even and odd harmonic frequencies begin to appear as a formal potential is moved. The closer the formal potential of the redox species of interest is to the switching potential, the more signal that appears in the higher harmonics relative to the fundamental.

Any condition that produces a sharper current versus time transition, will put more signal intensity into the higher frequencies. For example, increasing the number of electrons in a redox reaction will increase the current transient observed over a small potential window. This means that an n=2 redox couple will have more information in the higher harmonic frequencies. These data indicate that measurements made in the frequency domain may actually offer better selectivity than those in the time domain. For example, if two redox couples of different formal potentials are within the scan potential window, one could alter the potential window, that is change $E_{initial}$, $E_{switch}$ and the amplitude of sinusoid, to minimize the contributions of one redox couple at one harmonic frequency and maximize contribution of the other redox couple at the given harmonic frequency.

The phase angle of the measurement is another dimension that can be exploited to enhance selectivity and phase information can be directly related to the formal potential of the redox species.

Another electrochemical parameter that has a dramatic influence on the sinusoidal voltammetric frequency spectrum is the rate of electron transfer. Quasi-reversible and irreversible redox couples have drawn out voltammetric waves, where a three or four order of magnitude variation in $k^o$ can shift the diffusion limited peak currents several hundred millivolts. This corresponds to an increase in the relevant composition in the lower frequency harmonics in the frequency spectrum. While this is generally regarded as a problem in cyclic voltammetry, it can be used to a great advantage in the frequency spectrum to enhance the selectivity of this electrochemical measurement.

For example, the rate of electron transfer can be changed differentially for many electroactive species by several orders of magnitudes at carbon electrodes simply by changing the manner by which carbon surface is prepared. Many methods have been developed to change the density of electron transfer across a carbon surface. Mechanical polishing, electrochemical oxidation, radiofrequency oxygen plasma, microwave plasma, dispersion of metal oxide particles (i.e. alumina), in situ laser activation, and vacuum heat treatments have all been shown to increase the heterogeneous electron transfer rates for selected redox couples at carbon electrodes. Thus, simple electrode pretreatments may be used to dramatically change the frequency spectra of specific redox couples.

Therefore, it should be appreciated that the addition of kinetic control of the electronic transfer reaction to enhance the selectivity of the measurement may be much more easily implemented in this case than with conventional scanning electrochemical methods.

The invention thus has the ability to alter the selectivity of sinusoidal voltammetric measurement in that there are dramatic changes in the distribution of frequency elements of the voltammogram as a function of potential. Thus, it should be possible, particularly in a computer implemented embodiment, to pick a frequency and phase angle that is selected for a given redox couple, where the contribution of other redox reactions can be selectively ignored.

Additional improvements in the signal-to-noise ratio is due to the very narrow bandwidth of the lock-in amplifier. Thus, the signal from the potentiostat is passed to a lock-in amplifier that monitors the signal at one frequency, i.e. the fundamental frequency or one of its harmonics, at a specified phase angle. One can achieve high sensitivity with added selectivity by choosing the appropriate frequency to monitor and then optimizing the phase for the redox couple of interest.

As illustrated by comparison of FIGS. 6a and 6b to FIGS. 7a and 7b, very few surface redox waves are observed in the potential window normally used at a gold electrode. The more complex electrode surface, such as carbon, contains surface waves due to the redox chemistry of the surface functional groups (catechols/quinones) and absorbed species. While it is very difficult to isolate one faradaic process from the other background processes in the time domain, these redox processes can be more easily isolated in the frequency domain. A closer examination of the frequency spectra of the background processes at carbon electrodes shows that there are higher harmonic frequencies due to redox chemistry at these surface functionalities. While the magnitude of these background signals is over two orders of magnitude smaller than that due to the capacitive current, these signals will ultimately limit the sensitivity of the measurement. Fortunately, the frequency composition is significantly different from the diffusion limited faradaic current.

Thus, it becomes apparent that one can extract the faradaic current of interest from not only the charging current, but also other background currents by appropriate selection of a sine wave excitation frequency and monitoring at one of the signal harmonics at an appropriate phase angle. At the higher frequency harmonics, the faradaic signal can be as much as two orders of magnitude larger than the background, while the faradaic signal at the fundamental frequency is barely discernible.

Consider for example illustration of the methodology of the invention for analysis for biologically relevant molecules, such as the dopamine/ascorbate system. Ascorbate acts as an interferent when analyzing the stimulated release of neurotransmitters in the brain. The conventional method has been to use electrochemical activation of carbon fiber microelectrodes followed by a coating with a Nation film in fast scan cyclic voltammetry to discriminate the dopamine signal from the ascorbate signal. The use of electrochemical activation enhances the signal for dopamine while decreasing the signal for ascorbate, while Nafion, a cation exchange polymer, excludes anionic species, such as ascorbate, DOPAC and other acidic metabolites, while preconcentrating cationic species. Additionally, fast scan cyclic voltammetry discriminates the dopamine over the ascorbate by outrunning the kinetics of the ascorbate. The combination of these factors can provide over two orders of magnitude discrimination of dopamine over ascorbate.

Figure 8A:
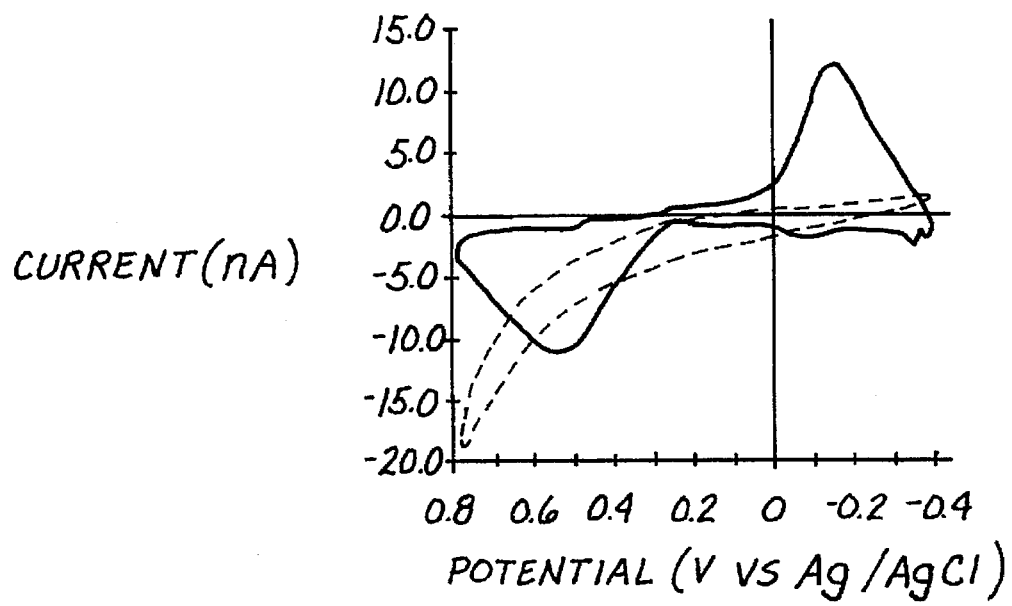
FIG. 8a is the background subtracted sinusoidal voltammograms for 30 microMolar dopamine shown in solid line and 250 microMolar ascorbic acid shown in dashed line at a scan frequency of 50 Hz at a 10 micron carbon fiber disk electrode in a phosphate/NaCl buffer with a pH of 7.4.
Figure 8B:
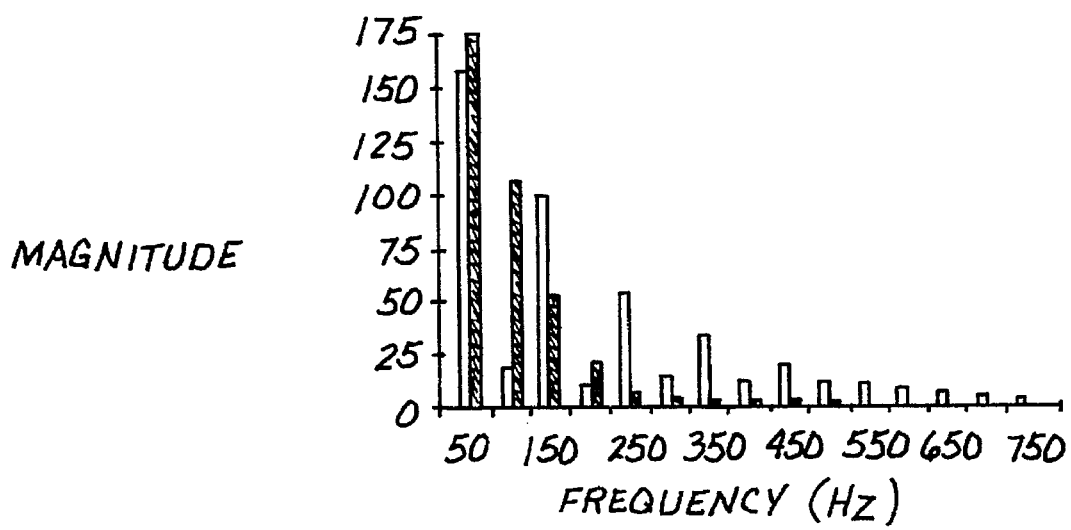
FIG. 8b shows the sinusoidal voltammetric signal of FIG. 8a in the frequency domain with the dopamine corresponding to the left bar and the ascorbic acid corresponding to the right bar of the histogram.

Sinusoidal voltammograms of 200 microMolar ascorbate and 4 microMolar dopamine are shown in FIG. 8a in dotted and solid lines respectively. There is little discrimination between oxidation of these two species at the bare carbon fiber surface, although slow electron transfer kinetics of ascorbate produces a large overpotential which reduces the current observed for ascorbate by a factor of 50. The power spectra of the high harmonics of both dopamine and ascorbate are shown in FIG. 8b in solid and hatched shading respectively. FIG. 8b illustrates that there is a considerable difference between the frequency spectrum of the dopamine and ascorbate signals, especially at the higher harmonics. Since the ascorbate signal virtually disappears by the fifth harmonic, while there is still a very large dopamine signal, there is considerable selectivity from measurements for dopamine at the higher harmonics. Indeed, the use of both frequency and phase selection can produce extremely high selectivity for the fast electron transfer species over species which exhibit slower kinetics.

The advantage of using the sinusoidal waveform and electrochemical analyzer becomes apparent when the technique is applied to the measurement of rapid, transient concentrations of electroactive active species. Typically, these measurements are performed in the prior art by measuring current at an electrode whose potential is set high enough to oxidize or reduce all components of interest. DC methods generally have given better sensitivity because the bandpass of the measurement was narrower, that is low pass filtering reduces high frequency noise.

Alternatively, when the potential excitation is a large amplitude sinusoid, the current output from the potentiostat is a distorted phase-shifted sine wave containing faradaic information at many frequencies. The signal from the potentiostat can be passed to a lock-in amplifier that monitors the signal at one frequency, i.e. the fundamental frequency of one of its harmonics, at a specified phase angle or the entire frequency spectrum of the response can be obtained by Fourier transform of the signal. By using a sinusoidal excitation waveform, the charging current is concentrated at the fundamental frequency, while a great deal of the faradaic current is transferred to higher harmonic frequencies. A much larger signal-to-background ratio is obtained by monitoring one of the harmonic frequencies, because the background current has minimal harmonic frequency composition. The use of a lock-in amplifier also increases the signal-to-noise ratio, because of the very narrow bandwidth of the instrument. Alternatively, the use of Fourier Transform methods allows discrimination of each individual frequency component and can be used to optimize single frequency methods. This also allows the measurement of many signals simultaneously, providing additional selectivity in the measurement. Thus, one can discriminate faradaic from background information by careful selection of both frequency and phase at which the current is monitored.

Figure 9A:
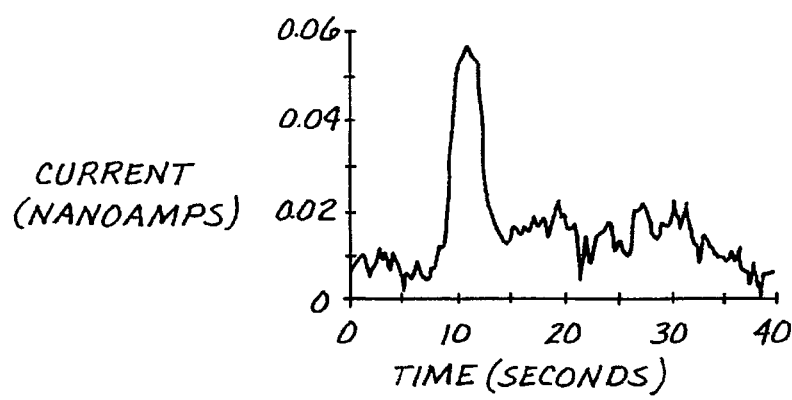
FIG. 9a is the sinusoidal lock-in detection response obtained using a lock-in amplifier in a flow injection analysis experiment for 1 nM hexamine ruthenium (III) chloride with the formal potential centered at the switching potential. The fifth harmonic was monitored at a phase angle of −112 degrees using an initial and switching potential equivalent to 0.9 V and −0.1 V versus Ag/AgCl respectively. A 32 micron carbon fiber was used as the electrode. The output filter on the lock-in amplifier was set to a cutoff frequency of 3 Hz.
Figure 9B:
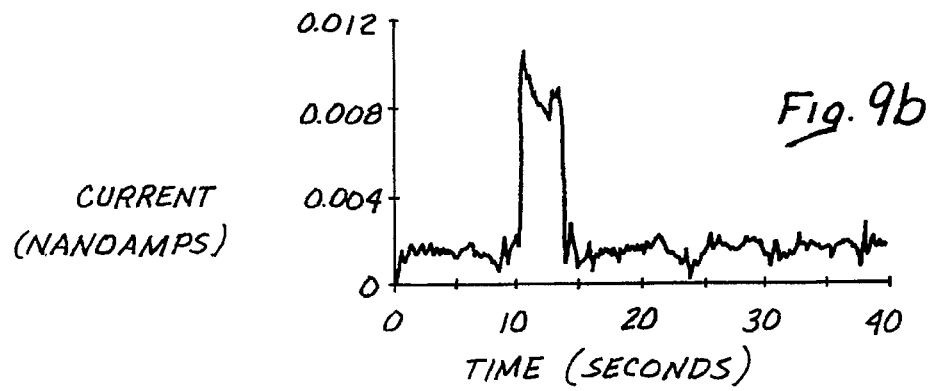
FIG. 9b is the DC amperometric response obtained in a flow injection analysis experiment using 250 nM hexamine ruthenium (III) chloride. The filter was set to a cutoff frequency of 2 Hz.

FIG. 9a shows a comparison of sinusoidal voltammetric lock-in detection as compared to DC amperometry illustrated in FIG. 9b. The flow injection analysis response is for micromolar hexamine ruthenium chloride as measured when locking in on the fifth harmonic at an optimized phased angle as shown in FIG. 9a. The DC amperometric response for 250 nM of ruthenium chloride is shown in FIG. 9b. The limited detection for hexamine ruthenium chloride is determined to be 200 pM using the sinusoidal voltammetric lock-in method and 20 nM using the DC amperometric method. Thus, the lock-in method offers a limit of detection approximately two orders of magnitude lower than DC amperometry.

Figure 10A:
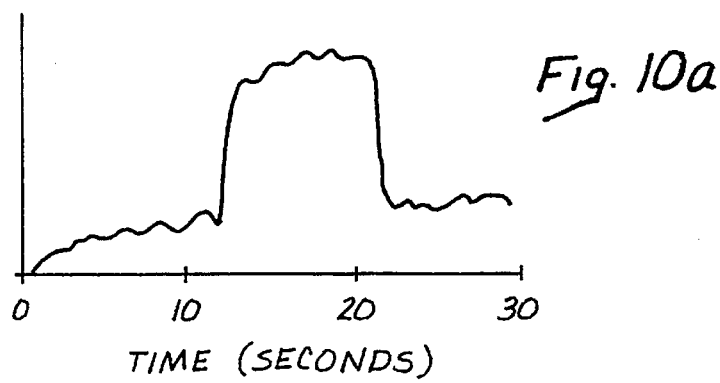
FIG. 10a is the DC amperometric response obtained in a flow injection analysis experiment of 1.4 microMolar dopamine. The applied potential is 0.8 V versus Ag/AgCl.
Figure 10B:
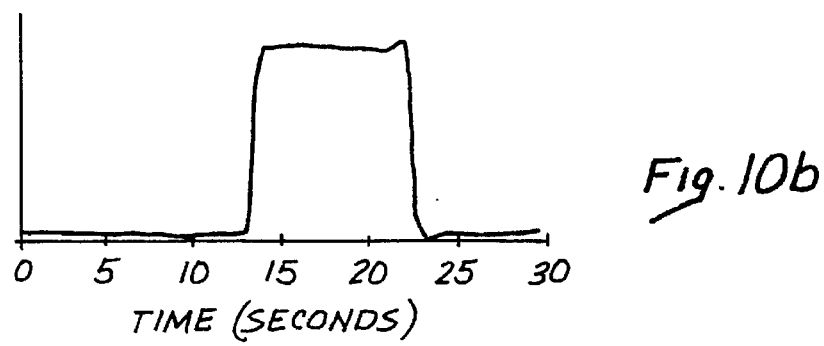
FIG. 10b is the DC amperometric response obtained in a flow injection analysis experiment of 200 microMolar ascorbate. The applied potential is 0.8 V versus Ag/AgCl.

The selectivity of this type of measurement is demonstrated in the discrimination of the dopamine response over the ascorbate signal. The DC amperometric response for 200 microMolar ascorbate and 4 microMolar dopamine is compared to the sinusoidal lock-in detection method as illustrated in FIGS. 10a and b. As expected, the magnitude of the DC amperometric signal for ascorbate as shown in FIG. 10b is approximately two orders of magnitude larger than that observed for dopamine in FIG. 10a.

Figure 11A:
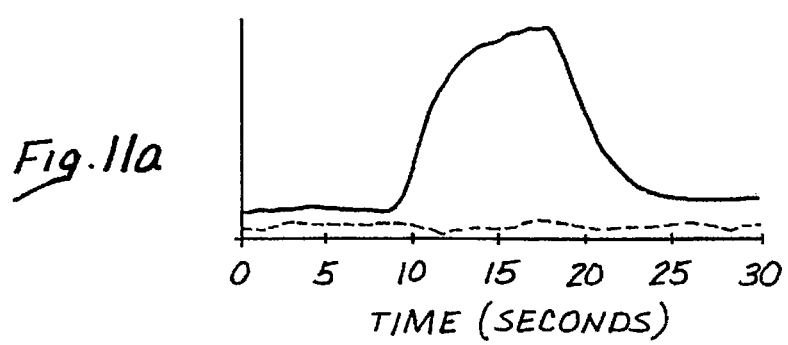
FIG. 11a is a comparison of the sinusoidal voltammetric lock-in detector response for 4 microMolar dopamine shown in solid line and 200 microMolar ascorbate shown in dotted line. The phase was optimized to 135 degrees at the fifth harmonic for dopamine to discriminate over ascorbate.

In contrast, as shown in FIG. 11a when a sinusoidal voltammetric waveform is used, the ascorbate signal is virtually gone by the fifth harmonic. Lock-in detection at this frequency (f=125 Hz) at a phase angle where the ascorbate signal was minimized, produces over three orders of magnitude discrimination of dopamine over ascorbate.

Figure 11B:
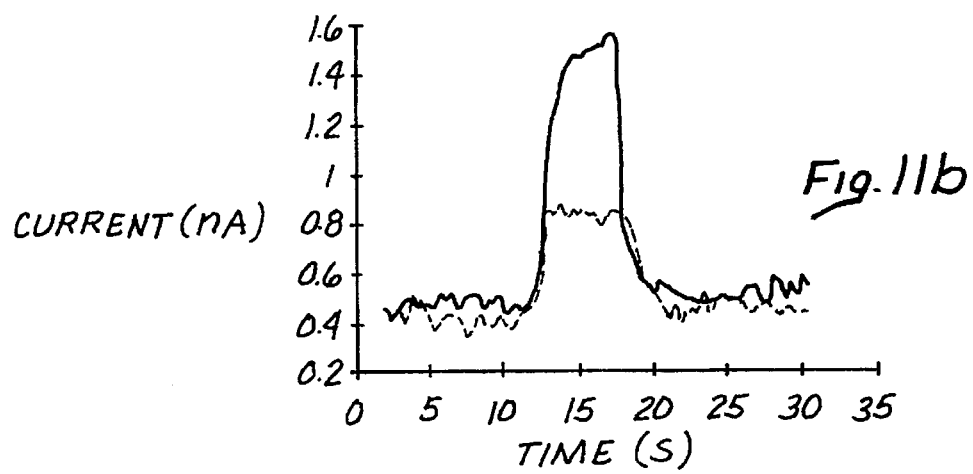
FIG. 11b is a comparison of the sinusoidal voltammetric lock-in response for 3 microMolar dopamine shown in solid line and 8 microMolar ascorbate shown in dotted line. The phase was optimized at the ninth harmonic for dopamine.

Even greater discrimination could be obtained at higher harmonics with some loss of sensitivity. For example, The ninth harmonic was monitored with a lock-in amplifier and the phase is optimized for the dopamine/ascorbic acid redox couple as shown in FIG. 11b. In this case, approximately four orders of magnitude better discrimination of dopamine over ascorbate was obtained compared to DC amperometric.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, the illustrated embodiment has described how large amplitude sinusoidal voltammetry can be used to discriminate between two small volume analytes. However, multiple analytes could be simultaneously subjected to the same or similar measurement with the current patterns or frequency spectra compared against a stored dictionary of patterns or spectra to identify the analytes using conventional software pattern analyses practiced in the context of either a single voltammetric measurement or a selectively controlled series of measurements.

Further, the illustrated embodiment has been described as being performed in a conventional flow injection analysis cell. However, the voltammetry can be performed in any environment including direct in vivo implantation of the measuring electrode, on-line detection in chromatography or electrophoretic apparatus. The invention includes the use of sinusoidal voltammetry with either lock-in detection or Fourier Transform based computer methods as an electroanalytical method for making fast, very small volume chemical analyses of a fluid.

Still further, the apparatus of the invention has been described as utilizing a lock-in amplifier as the means for selectively detecting the frequency and phase of the output current. It is expressly contemplated that many other equivalent means could be employed including digitizing of the output current from the potentiostat or electrode followed by appropriate digital filtering or other processing.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for making a fast electrochemical analysis in a voltammetric flow injection system of a small volume of analyte having at least one redox species of interest with a formal potential included within a potential window, the method comprising:

providing a small amount of said analyte in a flow to a voltammetric electrode;

applying a sinusoidal voltage characterized by a fundamental frequency to said electrode, said sinusoidal voltage having an amplitude large enough to sweep through said formal potential of said redox species of interest of said analyte in a single cycle at said fundamental frequency to generate a voltammetric response of said analyte to said sinusoidal voltage in a time domain; and generating a Fourier transform of said voltammetric response of said analyte to said sinusoidal voltage in said time domain to provide a spectrum of said voltammetric response in a frequency domain;

selectively quantifying said voltammetric response of said analyte to said sinusoidal voltage in said frequency domain at a harmonic of said fundamental frequency of said sinusoidal voltage rather than at said fundamental frequency without inversely transforming said voltammetric response back to said time domain to provide a quantitative analysis of said analyte, whereby a complete frequency spectrum is obtained within one cycle of said sinusoidal voltage.

2. The method of claim 1 where selectively quantifying said voltammetric response comprises selectively quantifying a current flowing through said analyte at said harmonic.

3. The method of claim 2 where quantifying said harmonic of said current detects only harmonics at and above a second harmonic of said fundamental frequency.

4. The method of claim 1 where selectively quantifying said voltammetric response comprises quantifying a plurality of higher harmonics of said fundamental frequency within a frequency spectrum of a current flowing through said analyte.

5. The method of claim 4 where quantifying said voltammetric response comprises quantifying harmonics within said frequency spectrum only at frequencies higher than a third harmonic of said fundamental frequency.

6. The method of claim 5 where selectively quantifying said voltammetric response comprises quantifying harmonics within said frequency spectrum only at a fifth harmonic and higher of said fundamental frequency of said current.

7. The method of claim 1 where said sinusoidal voltage has an initial potential and a switching potential defining bounds of said potential window and said method further comprises adjusting said potential window so that said formal potential of the redox species of interest of said analyte is set near said switching potential to thereby produce higher signal levels within higher harmonics of said fundamental frequency.

8. The method of claim 1 where selectively quantifing said voltammetric response comprises quantifying a current from said analyte at a selected phase angle of measurement to enhance a detected signal corresponding to said redox species of interest.

9. The method of claim 8 where selectively quantifying said voltammetric response comprises selecting a frequency of said sweeping sinusoidal voltage so that phase and frequency are both selected to enhance a detected signal corresponding to said redox species of interest of said analyte.

10. The method of claim 1 where selectively quantifying said voltammetric response comprises using a natural distortion of a rate of electron transfer between said analyte and said electrode to enhance a detected signal corresponding to said redox species of interest of said analyte.

11. The method of claim 10 wherein said electrode has a surface and/or composition and using a natural distortion of said rate of electron transfer is accomplished by specific preparation of said surface and/or composition of said electrode.

12. The method of claim 1 where selectively quantifying said voltammetric response comprises selecting a harmonic of said fundamental frequency of said sweeping sinusoidal voltage to enhance a detected signal corresponding to said redox species of interest of said analyte.

13. A method for making a fast electrochemical analysis of a small volume of analyte having at least one redox species of interest with a formal potential included within a potential window, the method comprising:

providing a small amount of said analyte to a voltammetric electrode;

applying a sinusoidal voltage characterized by a fundamental frequency to said electrode, said sinusoidal voltage having an amplitude large enough to sweep through said formal potential of said redox species of interest of said analyte in a single cycle at said fundamental frequency to generate a voltammetric response of said analyte to said sinusoidal voltage in a time domain; and generating a Fourier transform of said voltammetric response of said analyte to said sinusoidal voltage in said time domain to provide a spectrum of said voltammetric response in a frequency domain;

selectively quantifying said voltammetric response of said analyte to said sinusoidal voltage in said frequency domain at a harmonic of said fundamental frequency of said sinusoidal voltage rather than at said fundamental frequency without inversely transforming said voltammetric response back to said time domain to provide a quantitative analysis of said analyte, where said harmonic comprises at least one harmonic of said current above a third harmonic of said fundamental frequency, whereby a complete frequency spectrum is obtained within one cycle of said sinusoidal voltage.

* * * * *